(12) United States Patent
Dawkins et al.

(10) Patent No.: US 11,401,240 B2
(45) Date of Patent: Aug. 2, 2022

(54) PROCESS FOR THE SYNTHESIS OF LACTAMS

(71) Applicant: Conopco, Inc., Englewood Cliffs, NJ (US)

(72) Inventors: David Anthony Dawkins, Poynton (GB); Panagiotis Kotsakis, Athens (GR); Neil James Parry, Tarporley (GB); David William Thornthwaite, Little Neston (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 17/291,043

(22) PCT Filed: Oct. 23, 2019

(86) PCT No.: PCT/EP2019/078948
§ 371 (c)(1),
(2) Date: May 4, 2021

(87) PCT Pub. No.: WO2020/094403
PCT Pub. Date: May 14, 2020

(65) Prior Publication Data
US 2021/0395199 A1 Dec. 23, 2021

(30) Foreign Application Priority Data
Nov. 8, 2018 (EP) ..................................... 18205110

(51) Int. Cl.
*C07D 207/27* (2006.01)
(52) U.S. Cl.
CPC .................... *C07D 207/27* (2013.01)
(58) Field of Classification Search
CPC .................................................. C07D 207/27
See application file for complete search history.

(56) References Cited

U.S. PATENT DOCUMENTS

| 5,332,757 A | 7/1994 | Bird |
| 5,948,917 A | 9/1999 | Adachi |
| 9,586,901 B2 * | 3/2017 | Kumar .................... A61P 31/00 |
| 2003/0162924 A1 | 8/2003 | Vos et al. |

FOREIGN PATENT DOCUMENTS

| CN | 108658973 | 10/2018 |
| WO | WO2007030389 | 3/2007 |
| WO | WO2007085042 | 8/2007 |
| WO | WO2017029093 | 2/2017 |
| WO | WO2017029112 | 2/2017 |
| WO | WO2017029118 | 2/2017 |
| WO | WO2018091222 | 5/2018 |

OTHER PUBLICATIONS

Von R. Scheffold Und P. Dubs; Synthese von Azaprotoanemoninen; Helvetica Chimica Acta; 1967; pp. 798-808.
Kalaitzakis et al.; Methylene Blue as a Photosensitizer and Redox Agent: Synthesis of 5-Hydroxy-1H-pyrrol-2(5H)-ones from Furans; Angewandte Chemie; 2015; pp. 6283-6287; 54. issue.
Dittami et al.; Preparation of N-Alkyl Pyrrolidinones via Photocyclization of y-Keto-a,B-Unsaturated Amides; Tetrahedron letters; 1995; pp. 4197-4420; vol. 36 No. 24.
Search Report and Written Opinion in EP18205110; dated Feb. 15, 2019.
Search Report and Written Opinion in EP18205127; dated Apr. 18, 2019.
Search Report and Written Opinion in EP18205274; dated Apr. 18, 2019.
Search Report and Written Opinion in PCTEP2019078948; dated Nov. 26, 2019.
Search and Written Opinion in PCTEP2019078936; dated Mar. 11, 2020.
Search Report and Written Opinion in PCTEP2019080236; dated Mar. 11, 2020.
IPRP2 in PCTEP2019078936; dated Sep. 25, 2020.
Written Opinion in PCTEP2019078948; dated Oct. 7, 2020.
IPRP2 in PCTEP2019078948; dated Feb. 1, 2021.
Written Opinion in PCTEP2019080236; dated Sep. 18, 2020.

* cited by examiner

*Primary Examiner* — Kamal A Saeed
(74) *Attorney, Agent, or Firm* — Carter, DeLuca & Farrell LLP; George Likourezos

(57) ABSTRACT

A process for the synthesis of lactams suitable for use in antimicrobial, anti-biofilm and bacteriostatic compositions.

5 Claims, 2 Drawing Sheets

PROCESS FOR THE SYNTHESIS OF LACTAMS

The present invention relates to processes for the synthesis of lactams. The lactams are suitable for use in antimicrobial, anti-biofilm and bacteriostatic compositions.

WO 2017/029112 describes a method for the synthesis of particular lactams of interest.

Despite the methods disclosed therein, there is a need for further methods for the synthesis of lactams. In particular, owing to the usefulness of lactams in antimicrobial compositions, there is a need for improved methods for synthesis to facilitate production of lactams on a commercial scale, especially to increase yield and reduce impurities.

The present invention relates to improved methods for the synthesis of lactams for use in an antimicrobial composition.

In a first aspect, the present invention may provide a process for the synthesis of a lactam, the process comprising the steps of:
(a) an Aldol condensation between an acetone initiator and glyoxalic acid;
(b) treating the product(s) of step (a) with thionyl chloride;
(c) reacting the product of step (b) with ammonia or a primary amine, or salt thereof, to afford a lactam;
wherein step (c) involves addition of ammonia or a primary amine, or salt thereof, to the product of step (b).

DETAILED DESCRIPTION OF THE INVENTION

Figure 1:
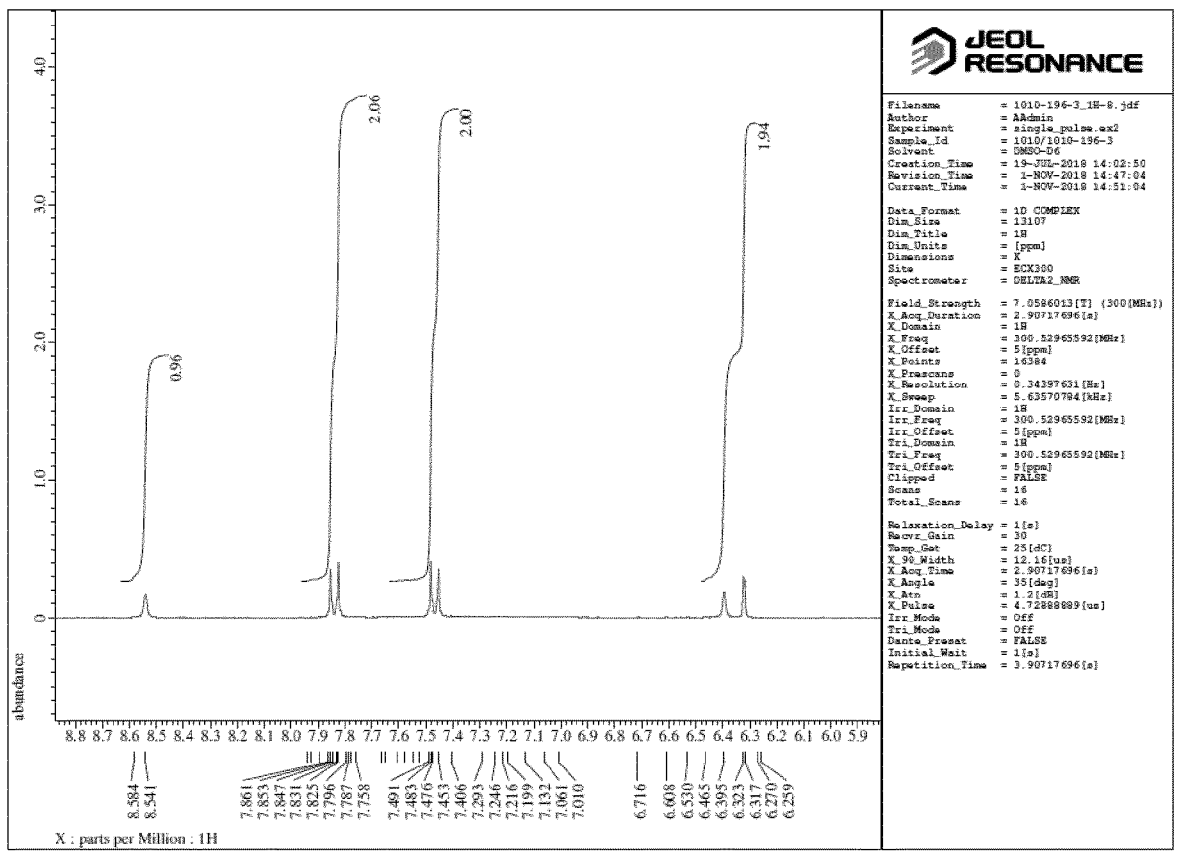
FIG. 1 relates to NMR spectra (filename 1010-196-3) of the product of step (c) wherein ammonia is added to the product of step (b). This is the method of the invention. This spectra doesn't show a large amount of polymer present as a broad peak in the aromatic region, and the integral of the product peaks is 2H as expected.

The indefinite article "a" or "an" and its corresponding definite article "the" as used herein means at least one, or one or more, unless specified otherwise.

It will be appreciated that, except where expressly provided otherwise, all preferences are combinable.

It will appreciated that starting materials, products and reagents may be used, where appropriate, as salts, hydrates and solvents thereof. Suitably, the glyoxalic acid is provided as the glyoxalic acid monohydrate.

Step (a) is an Aldol condensation. In other words, it is the reaction of two carbonyl containing compounds (the acetone initiator and the glyoxalic acid) to generate a β-hydroxy carbonyl compound that then dehydrates to give an α,β-unsaturated carbonyl compound. It may be thought of as an Aldol addition followed by dehydration.

In the reaction of step (a), this α,β-unsaturated carbonyl compound (product [A]) can then undergo cyclisation as shown below to give a lactone (product [B]) (substituents chosen for clarity, and not by way of limitation).

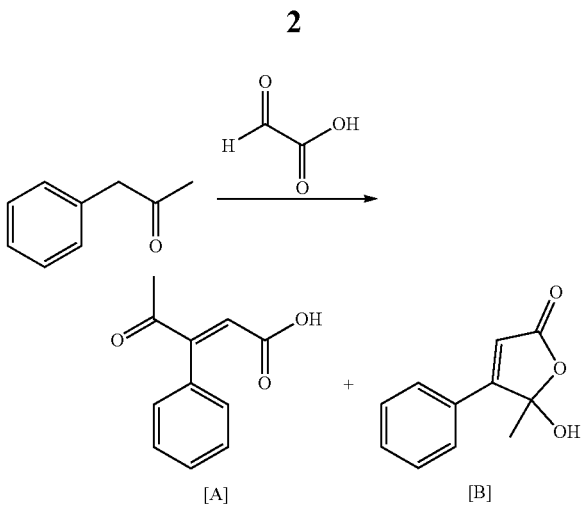

It will be appreciated that the ratio of [A] to [B] will depend on reaction conditions, but a mixture is typically obtained (with [A] as the major product, and [B] as the minor product). Of course, both [A] and [B] may be used separately.

It is not necessary to separate [A] and [B] to synthesise a lactam. Instead, the inventor(s) have found that, by using step (b) as claimed, both [A] and [B] can be used without separation.

Step (a) may be acid catalysed. In other words, step (a) may be an Aldol condensation between an acetone initiator and glyoxalic acid in the presence of an acid such as phosphoric acid ($H_3PO_4$) or an anhydride thereof (for example, $P_2O_5$).

The term "acetone initiator" as used herein refers to a compound having an acetone moiety. It may be substituted. Suitably, the acetone initiator is a compound of formula Ia:

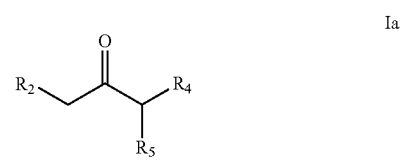

Ia wherein $R_2$, $R_4$, and $R_5$ are as defined herein with respect to Formula I and II or any subset herein defined.

For example, $R_2$ may be aryl or aralalkyl. Preferably, $R_2$ is an optionally substituted phenyl group, for example, an unsubstituted phenyl or mono-substituted phenyl group. Preferred substituents include halogen and methyl. For example, and without limitation, $R_2$ may be selected from phenyl, 4-fluorophenyl, 4-chlorophenyl, 4-bromophenyl and 4-methylphenyl.

Preferably, $R_4$ is H. Preferably, $R_5$ is H.

Accordingly, in some cases the acetone initiator is a 1-phenylpropan-2-one. For example, and without limitation, the acetone initiator may be 1-phenylpropan-2-one, 1-(4'fluorophenyl)propan-2-one, 1-(4'chlorophenyl)propan-2-one, 1-(4'bromophenyl)propan-2-one or 1-(4-tolyl)propan-2-one.

The product of step (a) is treated with thionyl chloride. Suitably the product of step (a) can be dissolved in thionyl chloride, and preferably heated, for example at a temperature above 50° C., for example between 50° C. and 80° C. The heating may be performed for a prolonged time, for example for 1 hr or more.

Prior to step (c), the reaction product of step (b) is preferably cooled.

The mixture may be concentrated and a solvent is suitably added. Exemplary solvents include toluene, and THF. A preferred solvent is 2-methyltetrahydrofuran.

Step (c) uses ammonia or a primary amine (in other words, an amine of formula $HNR_3$, where $R_3$ is as defined herein). Step (c) may be performed in solvent solution. Where $R_3$ is H (i.e. ammonia is used), the inventor(s) have found that a concentrated aqueous solution of ammonia may be used. A water-miscible co-solvent, for example a THF such as 2-methyltetrahydrofuran, may be added. A salt of said ammonia or primary amine may also be used, for example, the ammonia or primary amine may be provided as a solution in acetic acid (in which proton transfer will occur).

The lactam produced in step (c) is a 5-hydroxy-5-methyl-1H-pyrrol-2-one. Lactams having this structure are useful in antimicrobial compositions. However, the corresponding dehydrated products, that is, a 5-methylene-1H-pyrrol-2-one structure, are also useful in antimicrobial compositions.

Accordingly, the process may further comprise a step (d) which is dehydration of the lactam product of step (c) to afford a lactam having an exo-methylene group.

Previously described in WO 2017/029112, the reagent used in step (d) is boron trifluoride etherate, and the reaction was carried out in DCM.

The inventors of the present invention have improved this step (d) and found that using formic acid ($HCO_2H$) leads to a reaction product which includes fewer impurities when compared to the previous method using boron trifluoride etherate.

In some case, the lactam produced is a lactam of formula (I) or (II):

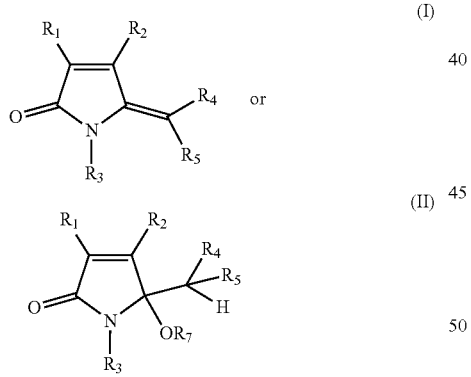

wherein:
$R_1$ and $R_2$ are each independently selected from hydrogen, halogen, alkyl, cycloalkyl, alkoxy, oxoalkyl, alkenyl, heterocyclyl, heteroaryl, aryl and aralalkyl; and
$R_3$ is selected from hydrogen, hydroxyl, alkyl, cycloalkyl, alkoxy, oxoalkyl, alkenyl, heterocyclyl, heteroaryl, cycloalkyl, aryl, aralalkyl and —$C(O)CR_6$=CH2;
$R_4$ and $R_5$ are independently selected from hydrogen, aryl, heterocyclyl, heteroaryl, and arylalkyl; and
$R_6$ is selected from hydrogen and methyl; and
$R_7$ is selected from hydrogen and —$C(O)CR_6$=$CH_2$; and
Preferably, at least one of $R_4$ and $R_5$ is hydrogen.

It will be appreciated that, where appropriate groups may be optionally substituted.

Optional substituents may include halogens, $C_{1-4}$alkyl, $C_{1-4}$haloalkyl (for example, $CF_3$) and $C_{1-4}$alkoxy.

Alkyls may, for example, be $C_{1-12}$alkyls, such as $C_{1-6}$alkyls. Aryls may, for example, be $C_{6-10}$aryls, for example, phenyls.

Preferably, at least one of $R_1$ and $R_2$ is selected from heterocyclyl, heteroaryl, aryl and arylalkyl; and Preferably, $R_1$ is hydrogen. Preferably, $R_3$ is hydrogen. Preferably, $R_4$ is hydrogen. Preferably, $R_5$ is hydrogen. Preferably, $R_6$ is hydrogen. Preferably, $R_7$ is hydrogen. Preferably, $R_2$ is aryl or arylalkyl. More preferably, $R_2$ is a phenyl group or a substituted phenyl group, for example, a mono-substituted phenyl group. Substitution may be ortho, meta, or para. Preferably, it is para. Preferred substituents include halogen and methyl. For example, and without limitation, $R_2$ may be selected from phenyl, 4-fluorophenyl, 4-chlorophenyl, 4-bromophenyl and 4-methylphenyl.

It will be appreciated that $R_3$ may be introduced through use of a primary amine of formula $HNR_3$ or, where $R_3$ is not H, through subsequent alkylation or similar of the pyrrolone. Accordingly, in some embodiments, the process comprises step (e), which may follow step (c), step (d), or step (f) (below), wherein the product of step (c), step (d) or step (f) is reacted with a compound of formula $R^3$-LG, wherein LG is a leaving group, for example, a halogen such as chloride or a OMs group. A base such as sodium methoxide may be present.

It will be appreciated that $R_7$ is selected from hydrogen and —$C(O)CR_6$=$CH_2$. In some cases, $R_7$ is hydrogen. In some cases $R_7$ is —$C(O)CR_6$=$CH_2$. In some cases $R_3$ is —$C(O)CR_6$=$CH_2$. In these latter two cases, the process may include a further step (f). Step (f) may follow step (c), step (d) or step (e) as appropriate.

Step (f), if present, comprises treating the product of step (c), step (d) or step (e) with an acryloyl chloride, for example, where $R_6$ is methyl, the acryloyl chloride is methacryloyl chloride.

Suitably, the reaction is performed dropwise in an inert solvent, for example, DCM at less than 5° C.

Preferred lactams may include:

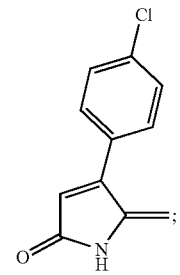

4-(4-chlorophenyl)-5-methylene-pyrrol-2-one (Ref. 488);

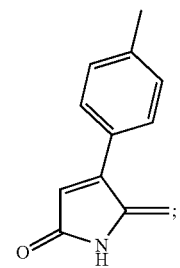

5-methylene-4-(p-tolyl)pyrrol-2-one (Ref. 491)

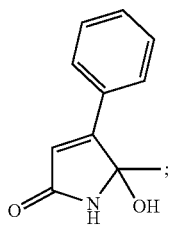

4-phenyl-5-hydroxy-5-methyl-1H-pyrrol-2-one (Ref. 131)

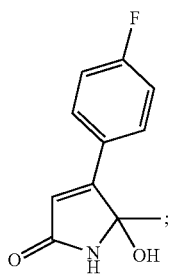

4-(4-fluorophenyl)-5-hydroxy-5-methyl-1H-pyrrol-2-one (Ref. 258)

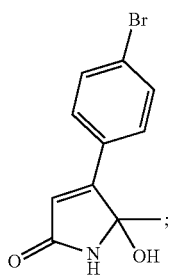

4-(4-bromophenyl)-5-hydroxy-5-methyl-1H-pyrrol-2-one (Ref. 318).

The acetone initiator may be commercially available. Where an acetone initiator is not commercially available, the following synthesis may be used. For both commercially available and non-commercially available acetone initiators, the invention may provide a process for making an acetone initiator, the process comprising:

(i) reacting an aldehyde with nitroethane; and
(ii) treating the product of step (i) with a Lewis acid.

This process may be combined with the process of the first aspect, before step (a).

For example, step (i) may comprise reaction of an optionally substituted benzaldehyde with nitroethane.

Suitably, step (i) is performed in refluxing ammonium acetate and acetic acid.

For step (ii), iron powder and iron trichloride may be used.

Compositions

The compositions described herein may be compositions having anti-microbial activity. In some cases, the compositions are anti-bacterial. They may have bactericidal and/or bacteriostatic activity. The inventor(s) have observed desirable bacteriostatic activity. Accordingly, in some cases, the composition is a bacteriostatic composition.

The compositions may also prevent and/or inhibit biofilm formation. Biofilms are formed when microorganisms stick to a surface. Biofilm extracellular polymeric substances may be formed. Biofilms (also referred to as slime) present problems in industrial environments; for example, they may form in pipes in apparatus, or industrial and agricultural structures, on solar panels, and on boat hulls and other marine structures. Biofilms may also pose a problem in domestic environments. For example, biofilms may form in domestic appliances such as washing machines. Biofilms are also present in personal care, for example, they may form on tooth surfaces.

Compositions suitable for any and all of these applications are within the scope of the invention. In some cases, the composition is a paint or other coating. In such cases, the composition may further comprise a binder, optionally a pigment and optionally one or more conventional additives (for example, to modify surface tension, improve flow properties, improve the finished appearance, increase wet edge, improve pigment stability, etc—such additives are known in the art). The composition may comprise an aqueous solvent or an organic solvent to suit purpose.

The composition may also be used in medical applications, for example to coat equipment including medical devices.

In some cases, the composition is a pharmaceutical composition. In other words, the composition may comprise a lactam as described herein and a pharmaceutically acceptable excipient. The composition may be suitable for topical use (for example, it may be a cream or lotion), it may be suitable for ocular use (for example, it may be an used as a pharmaceutical eye drop), it may be suitable for otic use (for example, it may be used as an ear drop), it may be suitable as a mouth wash, or it may be suitable for oral administration.

In some cases, the composition is a composition suitable for use in the home (often referred to as a homecare composition) or institutions. Homecare compositions include, without limitation, cleaning products, laundry detergents, and fabric conditioners. In some cases, the composition is a homecare composition, for example a laundry liquid. The composition may therefore comprise a detergent surfactant and a builder. The composition may be a fabric conditioner (also called a fabric softener) and may comprise an antistatic agent. The composition may also be a domestic cleaning product.

In some cases, the composition is a personal care composition. For example, the composition may be intended for use on the skin (for example, a cream, cleanser or serum). For example, the composition may be useful in the prevention or treatment of acne. For example, the composition may comprise one or more of dimethicone, petrolatum, a humectant such as hyaluronic acid or glycerin; and ceramide(s). In some cases, the composition is a personal care composition comprising a detergent, for example, the composition may be a face wash or shower gel or hair shampoo. The composition may be a hair treatment composition other than a shampoo. The composition may be a deodorant composition (for example, a deodorant powder, paste or liquid). The composition may be an oral care composition (such as a toothpaste or mouthwash and may include, for example, fluoride and/or flavourings.

In some cases, the composition is a contact lens cleaning fluid.

The composition may be a composition suitable for use in agriculture, for example, as a soil additive (solid or liquid).

The composition may be a composition suitable for use in the treatment of or manufacture of glass or lens for example as an additive/treatment for solar panels.

The compositions may also be used as additive compositions; in other words, the composition may be combined with further ingredients such as excipients to form a composition as described above.

It will be appreciated that, except where expressly provided otherwise, all preferences are combinable.

EXAMPLES

The following syntheses are provided by way of illustration and exemplification, and not by way of limitation.

Figure 3. Full synthetic route

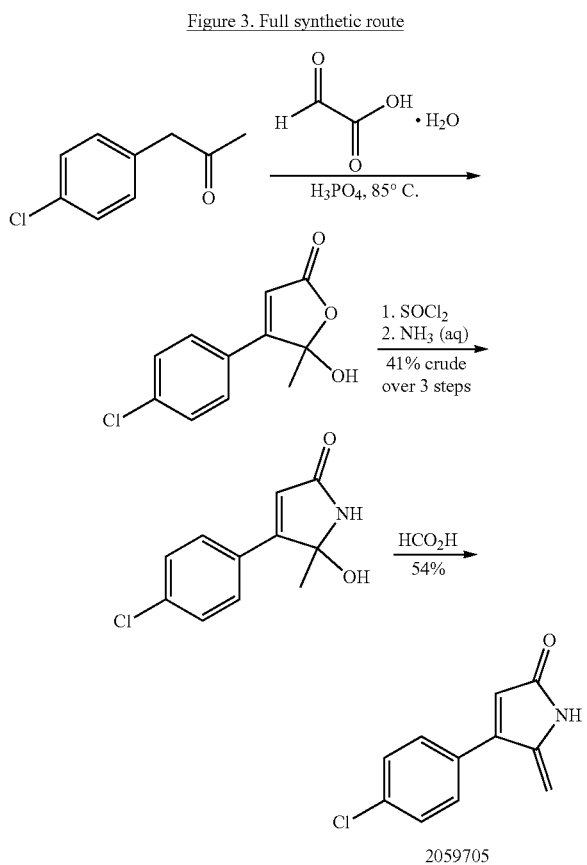

2059705

The full synthetic route is shown in FIG. 3. This synthetic route improves the overall yield from 6% to 22% in comparison to the synthetic route outlined in WO 2017/029112.

Preparation of 4-(4-chlorophenyl)-5-hydroxy-5-methylfuran-2(5H)-one

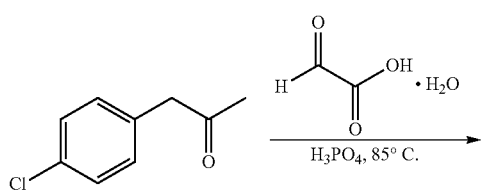

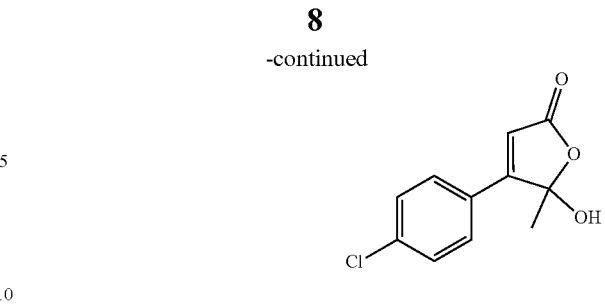

A mixture of 4-chlorophenylacetone (100 g, 0.59 mol), glyoxylic acid monohydrate (81.9 g, 0.89 mol) and crystallised phosphoric acid (174.5 g, 1.78 mol) was heated at 85° C. overnight. The reaction mixture was allowed to cool to 50° C. and ethyl acetate (1 L) then water (1 L) were added. On cooling to room temperature the organics were separated, washed with water (1 L) then brine (1 L), dried over magnesium sulphate and concentrated to give crude 4-(4-chlorophenyl)-5-hydroxy-5-methylfuran-2(5H)-one as a dark brown oil (287 g), which was used crude.

Preparation of 4-(4-chlorophenyl)-5-hydroxy-5-methyl-1H-pyrrol-2(5H)-one

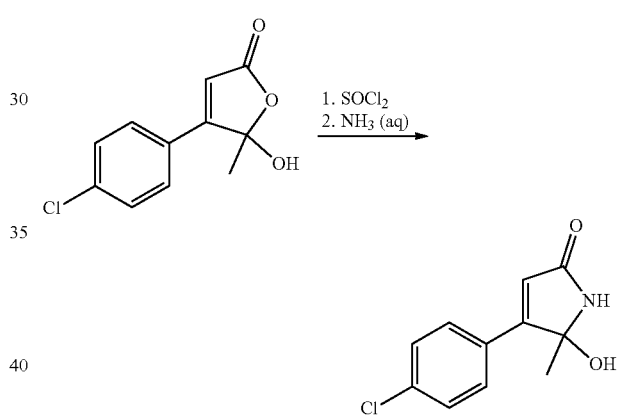

Crude 4-(4-chlorophenyl)-5-hydroxy-5-methylfuran-2 (5H)-one (287 g) was warmed to 50° C. and thionyl chloride (300 mL) was added portion-wise. Once addition was complete the reaction mixture was heated under reflux for 3 h, cooled to room temperature and concentrated to a dark oil. Toluene (2×300 mL) was added and the mixture concentrated further. The resultant dark oil was dissolved in tetrahydrofuran (1 L), cooled to 0° C. and 28% ammonium hydroxide (1 L) added over 1 h at 0-5° C. On complete addition the mixture was stirred for a further 1 h at 0-5° C. The mixture was then extracted with ethyl acetate (2×1 L). The combined extracts were washed with brine (1 L), stirred with silica and magnesium sulphate, filtered and concentrated to a dark oil. This was treated with tert-butylmethyl ether (250 mL) and the crude product filtered, washed with tert-butylmethyl ether (50 mL) and dried to give 4-(4-chlorophenyl)-5-hydroxy-5-methyl-1H-pyrrol-2(5H)-one as a light brown solid (54.1 g, 41% over 3 steps).

$^1$H NMR (300 MHz, DMSO-$d_6$) δ: 8.55 (brs, 1H), 7.85 (d, 2H), 7.48 (d, 2H), 6.36 (s, 1H), 6.34 (s, 1H), 1.45 (s, 3H).

The previous method described in WO 2017/029112 described addition of the intermediate to ammonia, whereas in this improved method, the ammonia is added to the intermediate. This change improved the yield as when the ammonia is added to the intermediate, the product contains minimal polymer in comparison with previous batches where the intermediate was added to ammonia. This is clear from the integrals in the aromatic region in the NMR spectra below.

Figure 2:
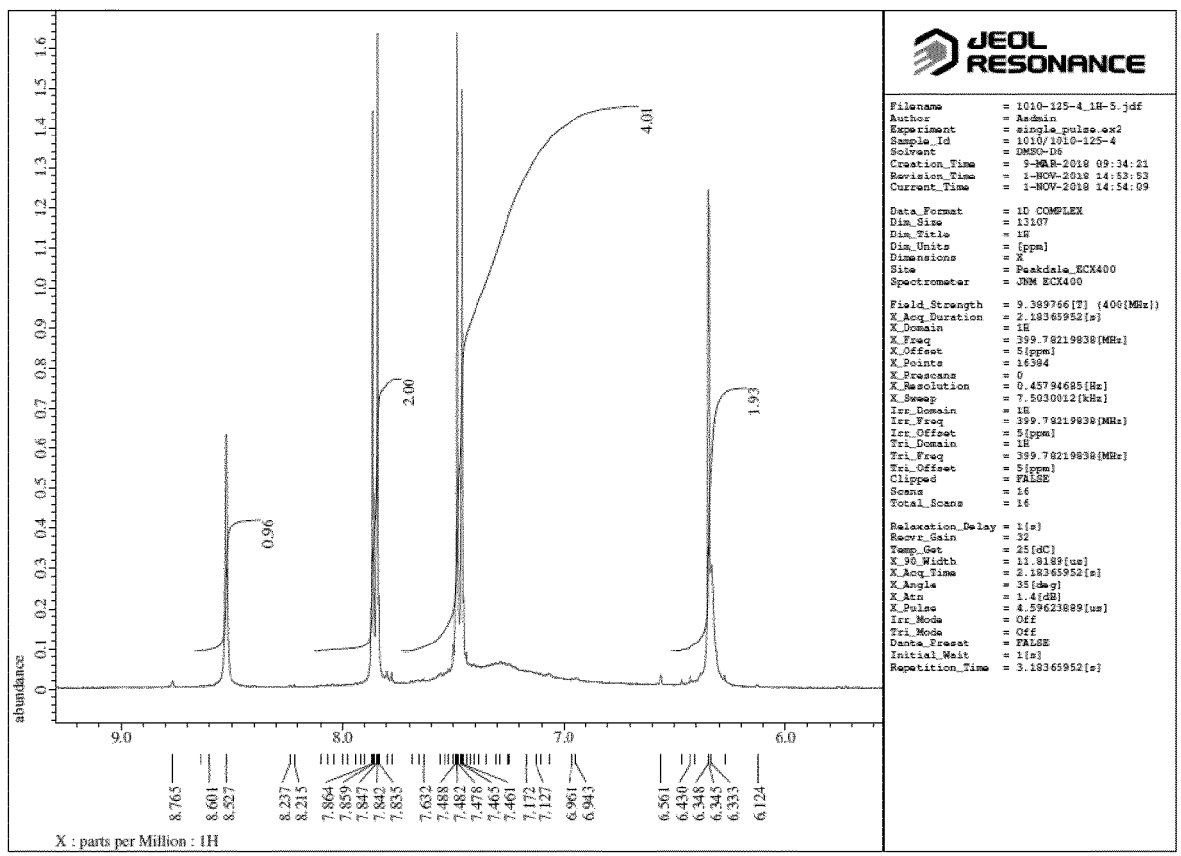
FIG. 2 relates to NMR spectra (filename 1010-125-4) of the product of step (c) wherein the product of step (b) is added to ammonia. This is the previous method disclosed in WO 2017/029112. This spectra shows a large amount of polymer present as a broad peak in the aromatic region. This is present under one of the product peaks so that the integral is ~4H rather than the expected 2H.

FIG. 2, the previous method from WO 2017/029112, shows a large amount of polymer present as a broad peak in the aromatic region. This is present under one of the product peaks so that the integral is ~4H rather than the 2H expected. The spectra from FIG. 1 was produced using the modified conditions (where the ammonia is added to the intermediate) and the amount of polymer is dramatically reduced so that the integrals are as expected. Improving this step massively increases the efficiency of the process because yield is much improved.

Preparation of 4-(4-chlorophenyl)-5-methylene-1H-pyrrol-2(5H)-one

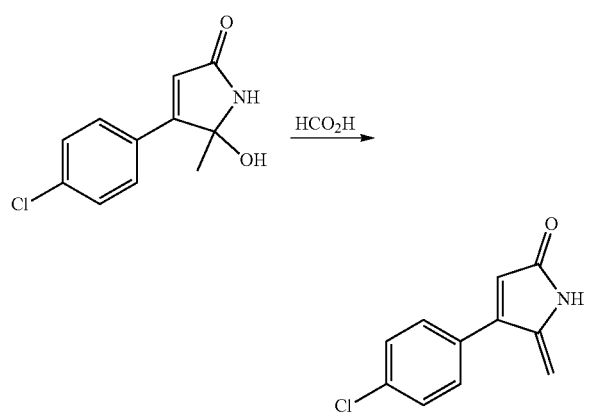

To formic acid (200 mL) was added 4-(4-chlorophenyl)-5-hydroxy-5-methyl-1H-pyrrol-2(5H)-one (20 g, 89.5 mmol). The resultant solution stirred for 3 h then poured into water (800 mL). The product was filtered, washed with water and dried to give 4-(4-chlorophenyl)-5-methylene-1H-pyrrol-2(5H)-one as a light brown solid (10.0 g, 54%).

$^1$H NMR (300 MHz, DMSO-$d_6$) δ: 10.20 (brs, 1H), 7.50 (m, 4H), 6.35 (s, 1H), 5.04 (s, 1H), 4.84 (s, 1H).

QNMR 94.64%

The previous method described in WO 2017/029112 described dehydration of the lactam product of step (c) to afford a lactam having an exo-methylene group via addition of boron trifluoride etherate in dichloromethane. Although the yield in this step was acceptable, it produces unwanted impurities in the final product.

The improved process step using formic acid instead of boron trifluoride etherate dramatically reduces the level of unwanted impurities.

Preparation of 5-hydroxy-5-methyl-4-(p-tolyl)furan-2(5H)-one

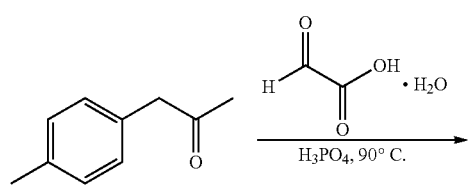

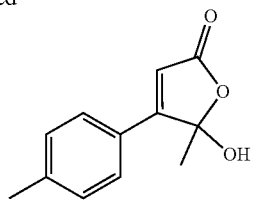

1-(p-Tolyl)propan-2-one (25.00 g, 24.00 mL, 168.7 mmol), glyoxylic acid monohydrate (23.29 g, 253.0 mmol) and phosphoric acid (49.60 g, 506.1 mmol) were combined at room temperature before heating at 90° C. overnight. After cooling to room temperature, the mixture was poured into a stirring mixture of ice-water (400 mL) and ethyl acetate (400 mL). The layers were separated and the organic phase washed with water (100 mL), dried (MgSO$_4$) and concentrated under reduced pressure. The mixture was azeotroped with 2-methyltetrahydrofuran (50 mL) to yield 5-hydroxy-5-methyl-4-(p-tolyl)furan-2(5H)-one (16.50 g, 48% yield) as a brown solid.

$^1$H NMR (400 MHz, $d_6$-DMSO) 7.86 (s, 1H), 7.75 (d, 2H), 7.28 (d, 2H), 6.59 (s, 1H), 2.32 (s, 3H), 1.61 (s, 3H)

In a similar fashion to the entire process described for the synthesis of 4-(4-chlorophenyl)-5-methylene-1H-pyrrol-2(5H)-one, the same process was used for the synthesis of 5-methylene-4-(p-tolyl)-1H-pyrrol-2(5H)-one.

The invention claimed is:

1. A process for the synthesis of a lactam, the process comprising:
    reacting an acetone initiator with a glyoxalic acid to produce an aldol condensate;
    treating the aldol condensate with thionyl chloride; and
    reacting the aldol condensate treated with thionyl chloride with ammonia or a salt thereof, to produce the lactam, wherein the reacting involves adding the ammonia or the salt thereof to the aldol condensate treated with thionyl chloride; wherein the acetone initiator is a compound with the formula:

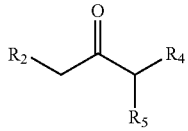

$R_2$ is 4-chlorophenyl, $R_4$ and $R_5$ are H, and
the lactam produced by the process is 4-(4-chlorophenyl)-5-methylene-pyrol-2-one represented by the formula:

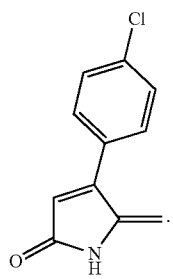

2. The process of claim 1, wherein the ammonia is concentrated aqueous ammonia.

3. The process of claim 1, wherein the process further comprises:
   dehydrating the lactam to produce a lactam having an exo-methylene group.

4. The process of claim 3, wherein the dehydrating is done with formic acid.

5. The process of claim 1, wherein the process further comprises, prior to reacting the acetone initiator with the glyoxalic acid:
   reacting an aldehyde with nitroethane; and
   treating the reacted aldehyde and nitroethane with a Lewis acid to produce the acetone initiator.

* * * * *